US007199251B2

(12) United States Patent
Kirchmeyer et al.

(10) Patent No.: US 7,199,251 B2
(45) Date of Patent: Apr. 3, 2007

(54) PROCESS FOR THE PRODUCTION OF LINEAR ORGANIC THIOPHENE-PHENYLENE OLIGOMERS

(75) Inventors: Stephan Kirchmeyer, Leverkusen (DE); Sergei Ponomarenko, Moskau (RU)

(73) Assignee: H.C. Starck GmbH & Co. KG, Goslar (DE)

( * ) Notice: Subject to any disclaimer, the term of this patent is extended or adjusted under 35 U.S.C. 154(b) by 316 days.

(21) Appl. No.: 10/984,513

(22) Filed: Nov. 9, 2004

(65) Prior Publication Data

US 2005/0098777 A1    May 12, 2005

(30) Foreign Application Priority Data

Nov. 12, 2003  (DE)  ................. 103 53 094

(51) Int. Cl.
*C07D 409/00* (2006.01)
(52) U.S. Cl. ...................................... 549/59
(58) Field of Classification Search .................. 549/59
See application file for complete search history.

(56) References Cited

U.S. PATENT DOCUMENTS

| 6,355,365 B1 | 3/2002 | Hotta et al. ................. 428/690 |
| 6,794,529 B2 | 9/2004 | Marcuccio et al. ......... 558/286 |
| 2003/0032838 A1 | 2/2003 | Marcuccio et al. ............ 562/7 |

FOREIGN PATENT DOCUMENTS

| EP | 439 627 A1 | 8/1991 |
| WO | 04/003108 | 1/2004 |

OTHER PUBLICATIONS

Handbook of Oligo- and Polythiophenes, (month unavailable) 1999, ed. by D. Fischou, pp. 469-471, "Oligothiophene FETs".
J. Heterocyclic Chem., 37, Jan.-Feb. 2000, S. Hotta et al, pp. 25-29 "Synthesis of Thiophene/Phenylene Co-oligomers. I Phenyl-capped Oligothiophenes".
Synthetic Metals 101, (month unavailable) 1999, pp. 551-552, S. Hotta et al, "Various chemical modifications of oligothienyls and oligophenyls".
Synthetic Metals, 106, (month unavailable) 1999, pp. 39-43, Sung Ae Lee et al, "Phenyl-capped oligothiophenes: novel light-emitting materials with different molecular alignments in thin films".
Chem. Mater., 13, (month unavailable) 2001, pp. 4686-4691, X. Michael Hong et al, "Thiophene-Phenylene and Thiophene-Thiazole Oligomeric Semiconductors with High Field-Effect Transistor On/Off Ratios".
Eur. Chem. J., 2, (month unavaile) 1996, pp. 1399-1406, Gerasimos M. Tsivgoulis et al, "Photoswitched and Functionalized Oligothiophenes: Synthesis and Photochemical and Electrochemical Properties".

Heterocycles, vol. 30, No. 1, (month unavailable) 1990, pp. 645-658, Salo Gronowitz et al, "Convenient Synthesis of Various Terheterocyclic Compounds by Pd(O)-Catalyzed Coupling Reactions".
J. Mater. Chem., 13, (month unavailable) 2003, pp. 1269-1273, Oliver Henze et al, "The synthesis and characterisation of amphiphilic α,α-linked sexithiophenes with substituents at the terminal α-positions".
J. Org. Chem., vol. 62, (month unavailable) 1997, pp. 6458-6459, Miki Murata et al, "Novel Palladium(O)-Catalyzed Coupling Reaction of Dialkoxyborane with Aryl Halides: Convenient Synthetic Route to Arylboronates".

(Continued)

*Primary Examiner*—Deborah C. Lambkin
(74) *Attorney, Agent, or Firm*—Connolly Bove Lodge & Hutz LLP

(57) ABSTRACT

The invention relates to a novel process for the production of linear organic thiophene-phenylene oligomers represented by the following general formula (I),

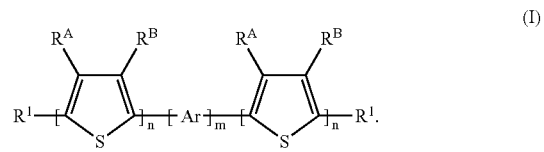

The process involves reacting (e.g., by means of a Suzuki coupling reaction) a compound represented by the following general formula (II),

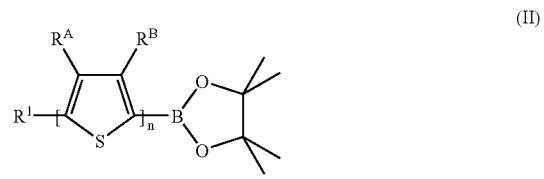

with a formula represented by the following general formula (III),

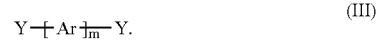

The reaction may be conducted optionally in the presence of catalysts, optionally in a solution and/or optionally at elevated temperature. The linear organic thiophene-phenylene oligomers of the present invention may be used to form semi-conductive coatings.

16 Claims, No Drawings

OTHER PUBLICATIONS

Journal of Organometallic Chemistry, 640, (month unavailable) 2001, pp. 197-199, Mohand Melaimi et al, "Bis(diphosphaferrocene) palladium(II) dimer complexes as efficient catalysts in the synthesis of arylboronic esters".

Chem. Commun., (month unavailable) 2000, pp. 1566-1567, Marjolaine Doux et al, "A $o^4$, $\lambda^5$-phosphinine palladium complex: a new type of phosphorus ligand and catalyst. Application to the Pd-catalyzed formation of arylbornic esters".

Tetrahedron Lett., 43, (month unavailable) 2002, pp. 5649-5651, Jun Takagi et al. "Iridium-catalyzed C-H coupling reaction of heteroaromatic compounds with bis(pinacolato)diboron: regioselective synthesis of heteroarylboronates".

J. Heterocyclic Chem., 37, Mar.-Apr. 2000, pp. 281-286, S. Hotta et al, "Synthesis of Thiophene/phenylene Co-oligomers. II [1]. Block and Alternating Co-oligomers".

Melucci, M. et al: "Solution-Phase Microwave-Assisted Synthesis of Unsubstituted and Modified .alpha.-Quinque- and Sexithiophenes Solution-Phase Microwave-Assisted Synthesis of Unsubstituted and Modified .alpha.-Quinque- Sexithiophenes" Journal of Organic Chemistry, 69(14), 4821-4828 Coden: Joceah; ISSN: 0022-3263, 2004, XP002319831.

Christophersen, Claus et al: "Synthesis of 2,3-Substituted Thienylboronic Acids and Esters Synthesis of 2,3-Substituted Thienylboronic Acids and Esters" Journal of Organic Chemistry, 68(24) 9513-9516 Coden: Joceah: Issn: 0022-3263, Oct. 31, 2003, XP002330210.

Patent Abstracts of Japan Bd. 016, Nr. 465 (E-1270) Sep. 28, 1992 & JP 04 164370 A (idemitsu Kosan Co Ltd), Jun. 10, 1992.

Sato T et al: "Photophysical Properties of Bis(2,2'-Bithiophene-5-YL)Benzenes" Journal of the Chemical Society. Faraday Transactions, Royal Society of Chemistry, Cambridge, GB, Bd. 94, Nr. 16, Aug. 21, 1998, Seiten 2355-2360, XP000776073.

Porzio W et al: "Organic FET devices: structure-property relationship in evaporated films of three fluorenone derivatives" Synthetic Metals, Elsevier Sequoia, Lausanne, CH, Bd. 146, Nr. 3, Nov. 3, 2004 Seiten 259-293, XP004629438.

Tirapattur S et al: "Spectroscopic Study of Intermolecular Interactions in Various Oligofluorenes: Precursors of Light-Emitting Polymers" Journal of Physical Chemistry, American Chemical Society, US; Bd. 106, 2002, Seiten 8959-3966, XP002321534.

PROCESS FOR THE PRODUCTION OF LINEAR ORGANIC THIOPHENE-PHENYLENE OLIGOMERS

CROSS REFERENCE TO RELATED PATENT APPLICATION

The present patent application claims the right of priority under 35 U.S.C. §119 (a)–(d) of German Patent Application No. 103 53 094.9, filed Nov. 12, 2003.

FIELD OF THE INVENTION

The invention relates to a novel process for the production of linear organic thiophene-phenylene oligomers, which are suitable for the production of semi-conductive coatings.

BACKGROUND OF THE INVENTION

The field of molecular electronics has developed rapidly in the last 15 years with the discovery of organic conductive and semi-conductive compounds. During this period, a large number of compounds exhibiting semi-conductive or electro-optical properties have been found. As well as oligothiophenes, thiophene-phenylene co-oligomers, for example, are also important representatives of the semi-conductive compounds. Compounds of this type are currently of great interest for areas of application such as organic field effect transistors (OFETs), organic light-emitting diodes (OLEDs), sensors and photovoltaic elements.

The production of thiophene-phenylene co-oligomers, also referred to below as thiophene-phenylene oligomers, can take place by various coupling reactions known to the person skilled in the art. The fact that the suitability of the end products for use in semiconductor technology depends substantially on their purity, and the disadvantageous effects of contaminated semiconductors on the properties, such as e.g. a poor on/off ratio in OFETs, of electronic applications produced therefrom, are generally known (Handbook of Oligo- and Polythiophenes, ed. by D. Fischou, Wiley-VCH, Weinheim, pp. 469–471).

Hotta et al. describe a series of phenylene oligothiophenes and their production via Grignard reactions or Suzuki coupling, but products are formed that are so strongly contaminated that high losses of yield are recorded after purification (J. Heterocyclic Chem. 2000, 37, 281–286; J. Heterocyclic Chem. 2000, 37, 25–29, Synt. Met. 1999, 101, 551–552). In all cases, the Suzuki coupling takes place between aryl boronic acids and thienyl halides. The suitability of oligothiophenes with phenyl units as terminal groups as light-emitting coating materials in OLEDs was described by Hotta et al. in Synt. Met. 1999, 106, 39–40.

Katz et al. recently described other thiophene-phenylene oligomers and their suitability as oligomeric semiconductors for OFETs. Unfortunately, here too, the most suitable, 1,4-bis(5-hexyl-2,2'-bithien-5-yl)phenyl, could only be produced in an extremely low yield of 10% by coupling of organotin thiophene compounds with dihaloaryl compounds, and so this method is unsuitable for the production of larger quantities of oligomers (Chem. Mater. 2001, 13, 4686–4691). Katz et al. also describe the synthesis of 1,4-bis(2,2'-bithien-5-yl)phenyl and 1,4-bis(4-hexyl-2,2'-bithien-5-yl)phenyl by Suzuki coupling of corresponding thiophene-phenylene-thiophene dihalides with monothiopheneboronic acids. However, it is a disadvantage of this method that a central thiophene-phenylene-thiophene dihalide unit has to be produced by complex coupling reactions. Moreover, thiopheneboronic acids are credited with low stability (Gronowitz et al., Heterocycles 1990, 30, 645–658; Lehn et al., Eur. Chem. J. 1996, 2, 1399–1406). Both result in high losses of yield and/or larger quantities of impurities.

In US-A 2002/0114973, other thiophene-phenylene oligomers are described, but the disadvantage still exists there that, with an increasing chain length, increasing numbers of coupling steps are needed to construct the molecule, which in turn leaves the problem of the high loss of yield and larger quantities of impurities, which have to be eliminated by means of complex, high-loss purification. US-A 2002/0114973 also describes the production of thiophene-phenylene oligomers by Grignard reactions and/or Suzuki coupling using thiopheneboronic acid.

A need exists, therefore, for a process for the production of semi-conductive organic thiophene-phenylene oligomers with which the end products are obtained in high purity and good yield via the fewest possible intermediates. Such a process for the production of these oligomers should advantageously be applicable regardless of their chain length.

SUMMARY OF THE INVENTION

The object of the present invention thus consisted in providing such a process. Surprisingly, it has now been found that a Suzuki coupling, in which a thiophene pinacoline boronic acid ester with more than one thiophene unit is used as the organoboron compound, meets these requirements.

The present invention thus provides a process for the production of compounds of the general formula (I),

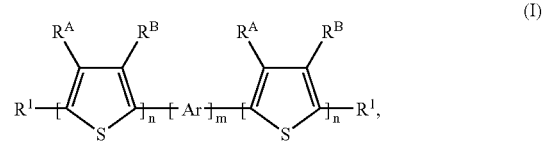

preferably using the Suzuki coupling wherein m denotes an integer from 1 to 5, preferably 1, 2 or 3, particularly preferably 1, Ar denotes optionally substituted 1,4-phenylene and/or 2,7-fluorenylene, $R^1$ denotes H or an optionally substituted linear or branched $C_1$–$C_{20}$ alkyl group, preferably a $C_1$–$C_{12}$ alkyl group, particularly preferably an ethyl, n-butyl, n-hexyl, n-octyl, n-decyl or n-dodecyl group or a linear $C_1$–$C_{20}$ alkyl group optionally interrupted by one or more O or S atoms, silylene, phosphonoyl or phosphoryl groups, preferably $C_1$–$C_{12}$ alkyl group or a $C_3$–$C_{20}$ alkenyl group, preferably a $C_1$–$C_{12}$ alkenyl group, particularly preferably an allyl, butenyl, pentenyl, hexenyl, heptenyl, octenyl, decenyl, undecenyl or dodecenyl group, $R^A$, $R^B$ independently of one another each denote H or a linear or branched $C_1$–$C_{20}$ alkyl group, optionally substituted and/or optionally interrupted with up to 10 oxygen atoms, preferably a $C_1$–$C_{12}$ alkyl group, particularly preferably a methyl, ethyl, propyl, butyl, pentyl or hexyl group, an optionally substituted $C_1$–$C_{20}$ alkoxy group, preferably a $C_1$–$C_6$ alkoxy group, particularly preferably a methoxy group, or together denote an optionally sub stituted $C_1-C_6$ dioxyalkylene group, e.g. a dioxyethylene group or dioxypropylene group, and n denotes 2, 3 or 4, characterised in that a compound of the general formula (II),

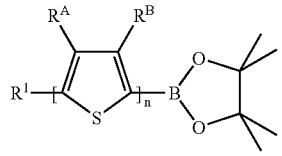
(II)

wherein n, $R^1$, $R^A$ and $R^B$ have the meaning given above for general formula (I), is reacted with a compound of the general formula (III),

(III)

optionally in the presence of catalysts, optionally in a solution and optionally at a higher temperature, wherein m and Ar have the meaning given for general formula (I) and Y denotes a rest Cl, Br, I or O—SO$_2$—$R^C$, with $R^C$ being a phenyl, tolyl, methyl or trifluoromethylrest.

The n thiophene units in the compounds of general formulae (I) or (II) can be the same or different, i.e. the substituents $R^A$ can be the same or different in the individual thiophene units and the substituents $R^B$ can be the same or different in the individual thiophene units. In other words, $R^A$ and $R^B$ are each selected independently for each n.

DETAILED DESCRIPTION OF THE INVENTION

In a preferred embodiment of the invention, $R^A$ and $R^B$ denote H.

In the event that $R^1$ denotes a $C_3-C_{20}$ alkenyl group, the double bond of the $C_3-C_{20}$ alkenyl group is preferably terminal (comp. e.g. formula II-a in example 1).

In general formulae (I) and (II) and in other formulae in this application, the structural formula of the pinacoline boronic acid residue

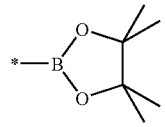

is to be understood as a simplified form of the structural formula

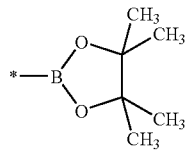

Suitable as substituents for the rest Ar are e.g. linear or branched $C_1-C_{20}$ alkyl residues, preferably $C_1-C_{12}$ alkyl residues, or linear $C_1-C_{20}$ alkyl residues interrupted by one or more O atoms. Optional substituents (one or more) on the 2,7-fluorenylene units preferably occupy the 9 position. Particularly preferred substituents for 1,4-phenylene rings are hydrogen, methyl, ethyl, propyl, butyl, pentyl or hexyl groups. Other particularly preferred substituents for 1,4-phenylene groups are methoxy, ethoxy, propoxy, butoxy, pentoxy, hexyloxy or heptyloxy groups. The especially preferred substituent is hydrogen.

The new process is preferably a process for the production of compounds of the general formula (I-a),

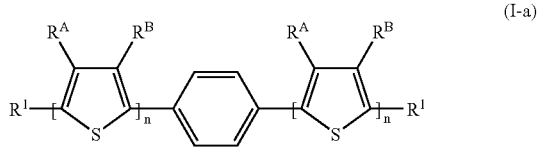
(I-a)

wherein n, $R^1$, $R^A$ and $R^B$ have the meaning given above for general formula (I), wherein a compound of general formula (II) is reacted with a compound of general formula (III-a),

(III-a)

wherein

Y has the meaning given above for general formula (III).

The following can be mentioned as examples of preferred compounds of general formula (I-a) produced according to the invention: 5-alkyl-5'-[4-(5'-alkyl-2,2'-bithien-5-yl)phenyl]-2,2"-bithiophene and 5-alkyl-5"-[4-(5"-alkyl-2,2':5',2"-terthien-5-yl)phenyl]-2,2':5',2"-terthiophene, especially 5-decyl-5"-[4-(5"-decyl-2,2':5',2"-terthien-5-yl)phenyl]-2, 2':5', 2"-terthiophene, 5-hexyl-5"-[4-(5"-hexyl-2,2':5',2"-terthien-5-yl)phenyl]-2,2':5', 2"-terthiophene, 5-ethyl-5"-[4-(5"-ethyl-2,2':5',2"-terthien-5-yl)phenyl]-2,2':5', 2"-terthiophene, 5-decyl-5'-[4-(5'-decyl-2,2'-bithien-5-yl) phenyl]-2,2"-bithiophene, 5-hexyl-5'-[4-(5'-hexyl-2,2'-bithien-5-yl)phenyl]-2,2"-bithiophene and 5-ethyl-5'-[4-(5'-ethyl-2,2'-bithien-5-yl)phenyl]-2,2"-bithiophene.

Such compounds are already generally described in U.S. Pat. No. 6,355,365 B1 and US 2002/0114973 A1. However, using the new process they can be obtained for the first time in particular purity, i.e. for example without contamination by homologous compounds or structural isomers, such as e.g. 3,5- and 2,4-linked thiophene units, and after a simple, one-step reaction of compounds of the general formula (II) with aryl dihalides. In US 2002/0114973, complex, multi-step processes are described for the production, which result in reduced yield and/or purity of the target compounds.

The process according to the invention is preferably carried out in a variant of Suzuki coupling. Suzuki coupling, i.e. the reaction of aryl halides and organoboron compounds, is described e.g. in Suzuki et al., Chem. Rev. 1995, 95, 2457–2483. In a preferred embodiment, the new process is carried out according to a variant of this Suzuki coupling, wherein aryl or heteroaryl halides and compounds of the general formula (I) are reacted, optionally in the presence of at least one base and/or at least one catalyst, which contains a metal of subgroup VIII of the periodic table, referred to below in shortened form as a metal of subgroup VIII.

The particularly preferred embodiment of the process (Suzuki coupling) is carried out at a temperature of +20° C. to +200° C., preferably of +40° C. to +150° C., particularly preferably of +80° C. to +130° C., in an organic solvent or solvent mixture.

As catalysts all suitable compounds containing a metal of subgroup VIII of the classification of elements, preferably Pd, Ni or Pt, particularly preferably Pd, can be considered in principle. The catalyst or catalysts are preferably used in quantities of 0.05 wt. % to 10 wt. %, particularly preferably 0.5 wt. % to 5 wt. %, based on the total weight of the compounds to be coupled.

Particularly suitable catalysts are complex compounds of metals of subgroup VIII, especially complexes of palladium (0), that are stable in air, Pd complexes that can be readily reduced with organometallic reagents (e.g. lithium alkyl compounds or organomagnesium compounds) or phosphines to form palladium(0) complexes, or palladium(2) complexes, optionally with the addition of PPh$_3$ or other phosphines. For example, PdCl$_2$(PPh$_3$)$_2$, PdBr$_2$(PPh$_3$)$_2$ or Pd(OAc)$_2$ or mixtures of these compounds with the addition of PPh$_3$ can be used. Pd(PPh$_3$)$_4$, which is available in an inexpensive form, is preferably used, with or without the addition of phosphines and, in a preferred embodiment without the addition of phosphines. PPh$_3$, PEtPh$_2$, PMePh$_2$, PEt$_2$Ph or PEt$_3$, particularly preferably PPh$_3$, is preferably used as the phosphines.

However, it is also possible to use palladium compounds without the addition of phosphine as catalysts, such as e.g. Pd(OAc)$_2$.

As the base, for example hydroxides, such as e.g. NaOH, KOH, LiOH, Ba(OH)$_2$, Ca(OH)$_2$, alkoxides, such as e.g. NaOEt, KOEt, LiOEt, NaOMe, KOMe, LiOMe, alkali metal salts of carboxylic acids, such as e.g. sodium, potassium or lithium carbonate, hydrogen carbonate, acetate, citrate, acetylacetonate, glycinate, or other carbonates, such as e.g. Cs$_2$CO$_3$ or Tl$_2$CO$_3$, phosphates, such as e.g. sodium phosphate, potassium phosphate or lithium phosphate, or mixtures of these can be used. Sodium carbonate is preferably used. The bases can be used as solutions in water or as suspensions in organic solvents, such as toluene, dioxane or DMF. Solutions in water are preferred, since the products obtained can be readily separated from the reaction mixture in this way, owing to their low solubility in water.

It is also possible to use other salts, such as e.g. LiCl or LiBr, as auxiliary substances.

In principle, all solvents or solvent mixtures that do not react with the pinacoline boronic acid esters of general formula (II) are suitable as the organic solvents. These are generally compounds having no halogen atoms or no hydrogen atoms that are reactive with respect to thiophene-pinacoline boronic acid esters. Suitable solvents are e.g. alkanes, such as pentane, hexane and heptane, aromatics, such as benzene, toluene and xylenes, compounds containing ether groups, such as dioxane, dimethoxyethane and tetrahydrofuran and polar solvents such as dimethylformamide or dimethyl sulfoxide. Aromatics are preferably used as solvents in the new process. Toluene is especially preferred. It is also possible to use mixtures of two or more of these solvents as the solvent.

The reaction mixture is worked up by methods that are known per se, e.g. by dilution, precipitation, filtration, extraction, washing, recrystallisation from suitable solvents, chromatography and/or sublimation. For example, working up can take place in that, after completion of the reaction, the reaction mixture is poured into a mixture of acidic (iced) water, e.g. prepared from 1 molar hydrochloric acid, and toluene, the organic phase is separated off, washed with water, the product obtained as a solid is filtered off, washed with toluene and then dried in a vacuum. The compounds of general formula (I) can be obtained in high quality and purity even without any further subsequent purification processes. However, it is possible to purify these products further by known methods, e.g. by recrystallisation, chromatography or sublimation.

The aryl dihalide compounds of general formula (III) used in this process can be produced by known processes or are commercially available. The production of the pinacoline boronic acid esters of general formula (II) is described e.g. in Feast et al., J. Mater. Chem. 2003, 13, 1269–1273, although organotin compounds are used as starting compounds here. Owing to their health risk, however, it would be advantageous to avoid the use of these organotin compounds.

Alternatively, the compounds of general formula (II) can be produced by various processes, which are known, in principle, to the person skilled in the art. For example, it is possible to produce the compounds of general formula (II) by reacting aryl halides and bis(pinacolato)diborane by metal-catalysed coupling, as described e.g. in WO-A 01/29051 A1 and Tetrahedron Lett. 2002, p. 5649. It is also possible to produce the compounds of general formula (II) by coupling oligothiophene halides with pinacolborane (J. Org. Chem. 1997, vol. 62, p. 6458; J. Organomet. Chem. 2001, vol. 640, p. 197; Chem. Commun. 2002, p. 1566). However, these reactions lead to products containing diaryls as by-products, which are difficult to separate from the pinacoline boronic acid esters of general formula (II) and particularly from the thiophene-phenylene oligomers of general formula (I) to be produced according to the invention.

The compounds of general formula (II) are therefore preferably produced by reacting organometallic compounds, e.g. organomagnesium compounds (e.g. Grignard compounds) or organolithium compounds, with pinacoline boronic acid esters. This is preferred in so far as, surprisingly, no diaryls are formed as by-products in this reaction.

The present invention also therefore provides a process for the production of the compounds of general formula (II),

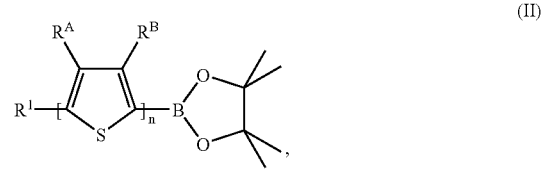

(II)

characterised in that compounds of general formula (IV),

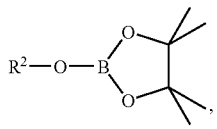

wherein $R^2$ denotes a linear or branched $C_1$–$C_{20}$ alkyl residue, are reacted with compounds of general formula (V)

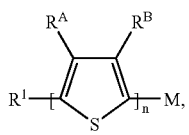

wherein n, $R^1$, $R^A$ and $R^B$ have the meaning given above for general formula (I) and M denotes LiX or MgX, wherein X denotes Cl, Br or I, preferably Br.

Preferred alkoxypinacoline boronic acid esters of general formula (IV) are those in which $R^2$ denotes a linear or branched $C_1$–$C_{12}$ alkyl residue, particularly preferably a rest of the group methyl, ethyl, n-propyl, i-propyl, n-butyl, t-butyl, i-butyl, n-pentyl or n-hexyl. In preferred embodiments of the process according to the invention, 2-isopropoxy-4,4,5,5-tetramethyl-1,3,2-dioxaborolane or methoxy-4,4,5,5-tetramethyl-1,3,2-dioxaborolane are used. These two compounds have the advantage that they are commercially available.

The process according to the invention is carried out in such a way that the reaction of the organometallic compounds of general formula (V) with the alkoxypinacoline boronic acid esters of general formula (IV) takes place at a temperature of −100° C. to +50° C., preferably −80° C. to +20° C., in an organic solvent or solvent mixture. Suitable as organic solvents or solvent mixtures are, in principle, all solvents or solvent mixtures that do not react with the compounds of general formulae (IV) and (V). These are generally solvents having no halogen atoms or no hydrogen atoms or carbonyl groups that are reactive with respect to organolithium compounds or Grignard compounds. Suitable solvents are, for example, alkanes, such as e.g. pentane, hexane and heptane, aromatics, such as e.g. benzene, toluene and xylenes, as well as compounds containing ether groups, such as e.g. diethyl ether, tert.-butyl methyl ether, dioxane and tetrahydrofuran. Solvents containing ether groups are preferably used in the process. Tetrahydrofuran is especially preferred. However, it is also possible to use mixtures of two or more of said solvents as the solvent. For example, mixtures of the preferably used solvent tetrahydrofuran and alkanes, e.g. hexane, can be used. Such mixtures can, for example, be contained in commercially available solutions of starting products, such as organolithium compounds.

The compounds of general formula (II) can be isolated from the reaction solution by known methods of working up, e.g. by simple filtration, and optionally further purified. Suitable purification methods are e.g. recrystallisation, sublimation or chromatography. The compounds of general formula (II) can be produced either in isolated form or directly in the reaction solution ("in situ") and employed without further working up.

The following can be mentioned as examples of compounds of general formula (II): 4,4,5,5-tetramethyl-2-[5'-(10-undecenyl)-2,2'-bithien-5-yl]-1,3,2-dioxaborolane (II-a), 2-(5''-decyl-2,2':5',2''-terthien-5-yl)-4,4,5,5-tetramethyl-1,3,2-dioxaborolane (II-b), 4,4,5,5-tetramethyl-2-[5'-hexyl-2,2'-bithien-5-yl]-1,3,2-dioxaborolane (II-c), 2-(5''-hexyl-2,2':5',2''-terthien-5-yl)-4,4,5,5-tetramethyl-1,3,2-dioxaborolane (II-d):

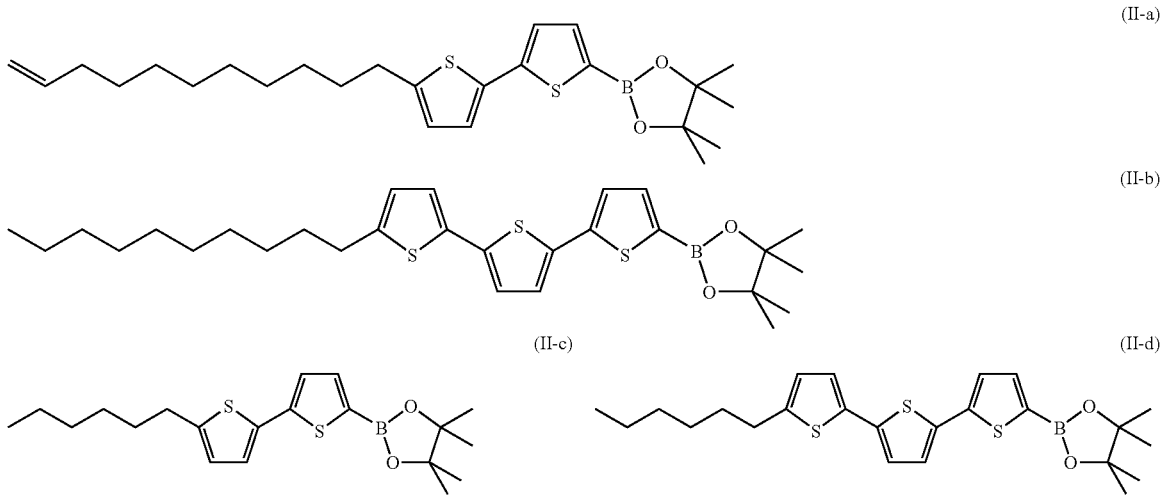

The starting compounds, such as Grignard or organolithium compounds of general formula (V), can be produced by known methods (cf. e.g. J. Mat. Chem. 2003, 13, 197) or are commercially available.

The compounds of general formula (II) are preferably obtained in a purity of at least 90%, particularly preferably of at least 95%.

The compounds of general formula (II) are distinguished by particular thermal stability and hydrolytic stability. They can be simply produced and isolated by the process according to the invention and are accessible in high purity, so that they are excellently suited as precursor molecules for the production according to the invention of semi-conductive thiophene-phenylene oligomers of general formula (I). Surprisingly, no deboronation takes place as a secondary reaction and the production according to the invention of the thiophene-phenylene oligomers can also be carried out under conditions such as e.g. in the presence of protic solvents, e.g. toluene-water mixtures, sodium carbonate as base and catalysed by tetrakis(triphenyl-phosphine)palladium, although it is known that thiopheneboronic acids, such as e.g. 2-thiopheneboronic acid, can hydrolyse rapidly under these conditions to form boric acid and thiophene and predominantly by-products are obtained (Chemica Scripta, 1984, 23, 120).

Thus, with the process according to the invention, it is possible for the first time to produce thiophene-phenylene oligomers of general formula (I) without any complex purification processes with only very small quantities of impurities. In particular, the compounds of general formula (I) produced according to the invention that are obtained are largely free from homologous oligomers with a higher or lower molecular weight that are difficult to separate off, and so it is unnecessary to perform a complex purification of mixtures that are difficult to separate.

The compounds of general formula (I) are preferably obtained in a purity of at least 95%, particularly preferably at least 99%.

The compounds of general formula (I) produced according to the invention are neutral and semi-conductive and, owing to their purity, are particularly suitable for use as semiconductors in active and light-emitting electronic components, such as field effect transistors, organic light-emitting diodes, photovoltaic cells, lasers or sensors. For this purpose, the compounds of general formula (I) produced according to the invention are applied in the form of coatings on to suitable substrates using solutions or the gasphase, e.g. on to silicon wafers, polymer films or panes of glass provided with electrical or electronic structures. In principle, all application processes known to the person skilled in the art are suitable for the application. For example, the compounds of general formula (I) can be applied from the gaseous phase by evaporation or sputtering of the compounds and then condensing on the substrate or from solution, in which case the solvent is then evaporated. Application from solution can take place by the known processes, e.g. by spraying, dipping, printing and knife coating, spin coating and by ink-jet printing. The compounds of general formula (I) are preferably applied from the gaseous phase, e.g. by vapour deposition. In this way, coatings with the smallest defects and highest charge mobilities can be obtained.

Semi-conductive coatings produced from the compounds produced according to the invention are distinguished by high purity and, consequently, small defects.

Thus, the present invention also provides coatings that contain the compounds of general formula (I) produced by the process according to the invention and are semi-conductive.

These are preferably coatings in which the compounds of general formula (I) are those of general formula (I-a),

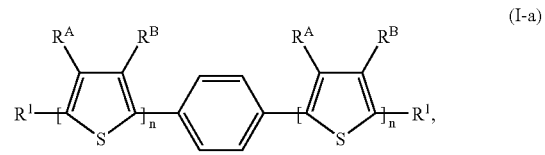

In preferred embodiments, the coatings according to the invention contain less than 0.5 wt. %, preferably less than 0.3 wt. %, particularly preferably less than 0.05 wt. % halogen.

The coatings according to the invention can be further modified after application, for example by heat treatment, e.g. passing through a liquid crystal phase, or for structuring purposes, e.g. by laser ablation.

Owing to their purity, the coatings according to the invention are excellently suited to use in active and light-emitting electronic components, such as field effect transistors, organic light-emitting diodes, photovoltaic cells, lasers or sensors.

EXAMPLES 5-(10-Undecenyl)-2,2'-bithiophene, 5-decyl-2,2':5',2''-terthiophene, 5-bromo-5'-ethyl-2,2'-bithiophene and 5-bromo-5''-ethyl-2,2':5',2''-terthiophene were produced by known processes (Synthesis, 1993, p. 1099; Chem. Mater., 1993, vol. 5, p. 430; J. Mater. Chem. 2003, vol. 13, p. 197).

Before use, all reaction vessels were baked out by a conventional protective gas technique and flooded with nitrogen.

Example 1

Production of 4,4,5,5-tetramethyl-2-[5'-(10-undecenyl)-2,2'-bithien-5-yl]-1, 3,2-dioxaborolane (II-a)

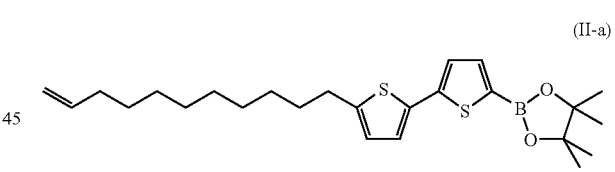

70 ml of anhydrous tetrahydrofuran (THF) were cooled to −74° C. using dry ice/acetone. 5.6 ml of a 2.5 M butyllithium solution in hexane were added to this dropwise using a syringe. A homogeneous mixture of 5-(10-undecenyl)-2,2'-bithiophene (4.46 g, 14 mmol) in 120 ml of anhydrous THF was then added dropwise and stirring continued for 30 min at −74° C. The cooling bath was removed, so that the temperature rose. At approx. 0° C., the reaction mixture was cooled again and 2-isopropoxy-4,4,5,5-tetramethyl-1,3,2-dioxaborolane (3.3 ml, 16 mmol) was added at −74° C. using a syringe. Stirring was continued at −74° C. for 30 min, the cooling bath was removed again and the temperature was allowed to increase to 20° C. The reaction mixture was added to 200 ml of ice-cooled water-mixed with 15 ml of 1 M HCl—and extracted with 500 ml of diethyl ether. The ether phase was separated off, washed with water, dried over $Na_2SO_4$, filtered and the solvent completely removed using a rotary evaporator. Yield: 6.03 g (97% of theoretical value) dark blue, crystalline product (II-a).

Analytical Data: GC MS analysis: M·+99%, m/e=444. $^1$H NMR (CDCl$_3$, TMS/ppm): 1.22–1.45 (overlapped peaks with a max. at 1.283, 14H), 1.345 (s, 12H), 1.672 (m, J=7.5 Hz, M=5, 2H), 2.037 (q, J=7.2 Hz, 2H), 2.781 (t, J=7.3 Hz, 2H), 4.928 (d, J=10.3 Hz, 1H), 4.991 (d, J=17.1 Hz, 1H), 5.811(m, 1H), 6.676 (d, J=3.4 Hz, 1H), 7.037 (d, J=3.9 Hz, 1H), 7.152 (d, J=3.9 Hz, 1H), 7.496 (d, J=3.4 Hz, 1H).

Example 2

Production of 2-(5″-decyl-2,2′:5′,2″-terthien-5-yl)-4,4,5,5-tetramethyl-1,3,2-dioxaborolane (II-b)

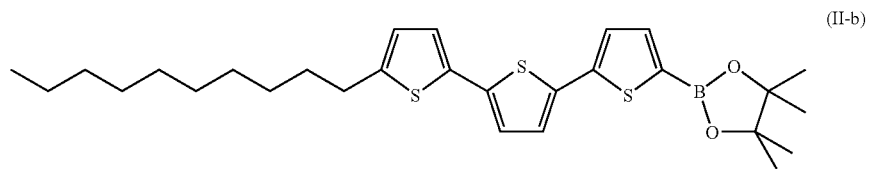

(II-b)

2-(5″-Decyl-2,2′:5′,2″-terthien-5-yl)-4,4,5,5-tetramethyl-1,3,2-dioxaborolane, 2.4 ml of a 2.5 M butyllithium solution in hexane, 5-decyl-2,2′:5′,2″-terthiophene (2.33 g, 6 mmol) and 2-isopropoxy-4,4,5,5-tetramethyl-1,3,2-dioxaborolane (1.4 ml, 7 mmol) are processed as described in Example 1 in 80 ml of anhydrous THF and the resulting product is isolated. Yield: 3.02 g (98% of theoretical value) olive-green, solid product (II-b).

Analytical Data: EI MS analysis: M·+ approx. 90%, m/e=514. $^1$H NMR (CDCl$_3$, TMS/ppm): 0.880 (3H, t, J=6.9 Hz), 1.20–1.45 (overlapped peaks, 14H), 1.351 (s, 12H), 1.678 (2H, m, J=7.5 Hz,), 2.787 (2H, t, J=7.6 Hz,), 6.679 (1H, d, J=3.4 Hz), 6.988 (2H, dd, J1=3.9 Hz, J2=3.9 Hz), 7.111 (1H, d, J=3.9 Hz), 7.209 (1H, d, J=3.9 Hz), 7.516 (1H, d, J=3.4 Hz).

Under protective gas, tetrakis(triphenylphosphine)palladium (Pd(PPh$_3$)$_4$ (46 mg, 0.04 mmol) was added to an initial charge of 1,4-dibromobenzene (142 mg, 0.6 mmol). A solution of 2-(5″-decyl-2,2′:5′,2″-terthien-5-yl)-4,4,5,5-tetramethyl-1, 3,2-dioxaborolane (II-b) (865 mg, 1.7 mmol) in 20 ml of anhydrous toluene and 5 ml of a 2 M aqueous Na$_2$CO$_3$ solution was prepared and deoxygenated with nitrogen. The two solutions were added to the reaction batch using syringes and the reaction mixture was then heated for 20 hours under reflux. After cooling, the reaction mixture was added to a mixture of 200 ml water, 80 ml 1 M HCl and 300 ml toluene. After shaking out three times with 100 ml water each time, the organic phase was filtered through a G4 glass filter and the filter residue was dried. Yield: 404 mg (79% of theoretical value) orange powder.

Analytical Data: EI MS analysis: Me·+99+%, m/e=850.3 EI MS analysis (after purification by sublimation at 0.25 mbar, 320° C.): M·+100%, m/e=850.3. Melt behaviour (° C.): K 310I (K=crystalline, I=isotropic liquid).

The melt behaviour was determined with a Mettler TA-4000 Thermosystem DSC (differential scanning calorimeter), scanning rate 10K/min.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for producing compounds represented by general formula (I),

Example 3

Production of 5-decyl-5″-[4-(5″-decyl-2,2′:5′,2″-terthien-5-yl)phenyl]-2, 2′:5′,2″-terthiophene (I-a-1)

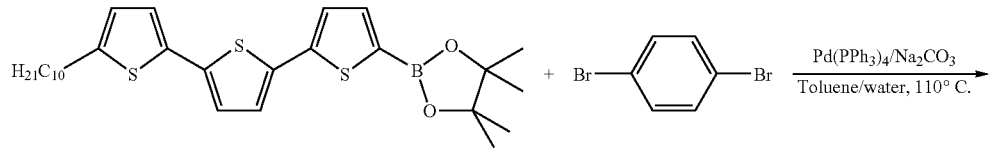

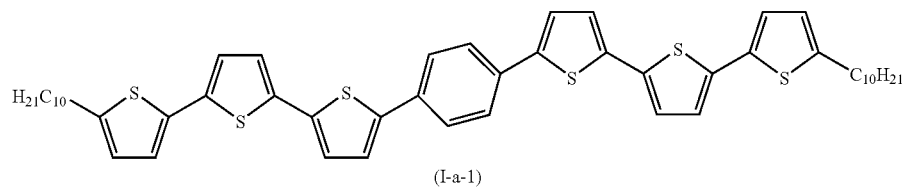

(I-a-1)

(I)

$$R^1\text{---}[\underset{S}{\underset{|}{\overset{R^A \quad R^B}{\diagdown\diagup}}}]_n\text{---}[Ar]_m\text{---}[\underset{S}{\underset{|}{\overset{R^A \quad R^B}{\diagdown\diagup}}}]_n\text{---}R^1$$

wherein,
  m denotes an integer from 1 to 5,
  Ar denotes a member selected from the group consisting of 1,4-phenylene and 2,7-fluorenylene, in each case optionally substituted with a member selected from the group consisting of linear or branched $C_1$–$C_{20}$ alkyl residues, and linear $C_1$–$C_{20}$ alkyl residues interrupted by at least one O atom,
  $R^1$ denotes a member selected from the group consisting of H, linear or branched $C_1$–$C_{20}$ alkyl groups, linear $C_1$–$C_{20}$ alkyl groups interrupted by at least one O atom, linear $C_1$–$C_{20}$ alkyl groups interrupted by at least one S atom, silylene groups, phosphonoyl groups, phosphoryl groups, and $C_3$–$C_{20}$ alkenyl groups,
  $R^A$, $R^B$ independently of one another, and independently for each n, are each selected from the group consisting of H, a linear or branched $C_1$–$C_{20}$ alkyl group, a linear or branched $C_1$–$C_{20}$ alkyl group interrupted with 1 to 10 oxygen atoms, a $C_1$–$C_{20}$ alkoxy group, and together form a $C_1$–$C_6$ dioxyalkylene ring, and
  n denotes 2, 3 or 4,
said process comprising reacting,
  a compound represented by general formula (II), (II)

$$R^1\text{---}[\underset{S}{\underset{|}{\overset{R^A \quad R^B}{\diagdown\diagup}}}]_n\text{---}B\underset{O}{\overset{O}{\diagdown\diagup}}\diagup\diagdown$$

wherein,
  n, $R^1$, $R^A$ and $R^B$ are each as described in general formula (I),
with a compound represented by general formula (III), (III)

$$Y\text{---}[Ar]_m\text{---}Y$$

wherein,
  m and Ar are each as described in general formula (I), and
  Y denotes a member selected from the group consisting of Cl; Br; I; and O—$SO_2$—$R^C$, in which $R^C$ represents a phenyl, tolyl, methyl or trifluoromethyl,
said reaction being performed,
  optionally in the presence of catalysts,
  optionally in a solution, and
  optionally at an elevated temperature.

2. The process of claim 1 wherein the compound produced by said process is represented by general formula (I-a), (I-a)

$$R^1\text{---}[\underset{S}{\underset{|}{\overset{R^A \quad R^B}{\diagdown\diagup}}}]_n\text{---}\bigcirc\text{---}[\underset{S}{\underset{|}{\overset{R^A \quad R^B}{\diagdown\diagup}}}]_n\text{---}R^1$$

wherein
  n, $R^1$, $R^A$ and $R^B$ have the meaning given in claim 1,
said process comprising reacting the compound represented by general formula (II) with a compound represented by general formula (III-a), (III-a)

$$Y\text{---}\bigcirc\text{---}Y.$$

3. The process of claim 2 wherein the compound represented by formula (Ia) is selected from the group consisting of  5-alkyl-5'-[4-(5'-alkyl-2,2'-bithien-5-yl)phenyl]-2,2''-bithiophene and 5-alkyl-5''-[4-(5''-alkyl-2,2':5',2''-terthien-5-yl)phenyl]-2,2':5', 2''-terthiophene, especially 5-decyl-5''-[4-(5''-decyl-2,2':5',2''-terthien-5-yl)phenyl]-2,2':5', 2''terthiophene, 5-hexyl-5''-[4-(5''-hexyl-2,2':5',2''-terthien-5-yl)phenyl]-2,2':5', 2''-terthiophene, 5-ethyl-5''-[4-(5''-ethyl-2,2':5',2''-terthien-5-yl)phenyl]-2,2':5', 2''-terthiophene, 5-decyl-5'-[4-(5'-decyl-2,2'-bithien-5-yl)phenyl]-2,2''-bithiophene, 5-hexyl-5'-[4-(5'-hexyl-2,2'-bithien-5-yl)phenyl]-2,2''-bithiophene and 5-ethyl-5'-[4-(5'-ethyl-2,2'-bithien-5-yl)phenyl]-2,2''-bithiophene.

4. The process of claim 1 wherein $R^A$ and $R^B$ each denote H.

5. The process of claim 1 wherein the reaction takes place in the presence of at least one catalyst containing a metal selected from the group consisting of subgroup VIII of the periodic table.

6. The process of claim 1 wherein said reaction is performed in the presence of at least one base.

7. The process of claim 1 wherein said reaction is performed in the presence of at least one organic solvent.

8. A process for producing a compound represented by general formula (II), (II)

$$R^1\text{---}[\underset{S}{\underset{|}{\overset{R^A \quad R^B}{\diagdown\diagup}}}]_n\text{---}B\underset{O}{\overset{O}{\diagdown\diagup}}\diagup\diagdown,$$

wherein,
  $R^1$ denotes a member selected from the group consisting of H, linear or branched $C_1$–$C_{20}$ alkyl groups, linear $C_1$–$C_{20}$ alkyl groups interrupted by at least one O atom, linear $C_1$–$C_{20}$ alkyl groups interrupted by at least one S atom, silylene groups, phosphonoyl groups, phosphoryl groups, and $C_3$–$C_{20}$ alkenyl groups,
  $R^A$, $R^B$ independently of one another, and independently for each n, are each selected from the group consisting of H, a linear or branched $C_1$–$C_{20}$ alkyl group, a linear or branched $C_1$–$C_{20}$ alkyl group interrupted with 1 to 10 oxygen atoms, a $C_1$–$C_{20}$ alkoxy group, and together form a $C_1$–$C_6$ dioxyalkylene ring, and n denotes 2, 3 or 4, said process comprising reacting a compound represented by general formula (IV),

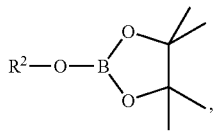 (IV)

wherein $R^2$ denotes a linear or branched $C_1$–$C_{20}$ alkyl residue, with a compound represented by general formula (V),

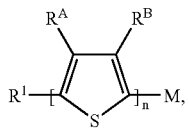 (V)

wherein $R^A$, $R^B$, $R^1$ and n are as described in formula (II), and M denotes LiX or MgX, wherein X denotes Cl, Br or I.

9. The process of claim 8 wherein the formula represented by formula (II) is selected from the group consisting of 4,4,5,5-tetramethyl-2-[5'-(10-undecenyl)-2,2'-bithien-5-yl]-1,3,2-dioxaborolane (II-a), 2-(5''-decyl-2,2':5',2''-terthien-5-yl)-4,4,5,5-tetramethyl-1,3,2-dioxaborolane (II-b), 4,4,5,5-tetramethyl-2-[5'-hexyl-2,2'-bithien-5-yl]-1,3,2-dioxaborolane (II-c), and 2-(5''-hexyl-2,2':5',2''-terthien-5-yl)-4,4,5,5-tetramethyl-1,3,2-dioxaborolane (II-d).

10. The process of claim 1 wherein said compound (II) is prepared by the process of claim 8.

11. A semi-conductive coating comprising the compound (I) produced by the method of claim 1.

12. An article of manufacture comprising at least one coating layer comprising the compound (I) of claim 1, wherein said article of manufacture is selected from the group consisting of active electronic components, light-emitting electronic components, field effect transistors, organic light-emitting diodes, photovoltaic cells, lasers and sensors.

13. A process for producing the article of manufacture of claim 12 comprising:

providing a substrate; and applying a coating composition comprising the compound (I) of claim 1 to said substrate.

14. The process of claim 13 wherein said coating composition further comprises solvent, and said process further comprises evaporating the solvent from said coating composition after it is applied to said substrate.

15. The process of claim 13 further comprising converting said coating composition into the gaseous phase, and condensing the gaseous phase coating composition to said substrate.

16. The process of claim 13 wherein the application step comprises sputtering said coating composition onto said substrate, and said process further comprises condensing the sputtered coating composition on said substrate.

* * * * *